United States Patent
Chang et al.

(10) Patent No.: US 7,758,900 B2
(45) Date of Patent: *Jul. 20, 2010

(54) MULTI-PART SUBSTITUTION INFUSION FLUIDS AND MATCHING ANTICOAGULANTS

(75) Inventors: Peter C. Chang, Leiden (NL); Jean-Michel Lannoy, Anstaing (FR)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/678,525

(22) Filed: Feb. 23, 2007

(65) Prior Publication Data

US 2007/0134348 A1 Jun. 14, 2007

Related U.S. Application Data

(63) Continuation of application No. 10/742,137, filed on Dec. 19, 2003, now Pat. No. 7,186,420, which is a continuation-in-part of application No. 09/959,543, filed as application No. PCT/EP00/03583 on Apr. 20, 2000, now Pat. No. 6,743,191.

(30) Foreign Application Priority Data

Apr. 26, 1999 (EP) .................................. 99201302

(51) Int. Cl.
*A61K 33/06* (2006.01)
*A61K 33/00* (2006.01)
*A61K 33/20* (2006.01)
*A61K 33/42* (2006.01)
*A61M 1/34* (2006.01)

(52) U.S. Cl. ................ 424/682; 424/601; 424/602; 424/663; 424/678; 424/679; 424/680; 424/681; 514/822; 210/647

(58) Field of Classification Search ................ 210/647; 424/601, 602, 606, 663, 677, 678, 679, 680, 424/681, 682, 722; 435/2; 514/822
See application file for complete search history.

(56) References Cited

U.S. PATENT DOCUMENTS 3,962,075 A * 6/1976 Fialkoff et al. .............. 210/641

(Continued)

FOREIGN PATENT DOCUMENTS

DE 4122754 A1 1/1993

(Continued)

OTHER PUBLICATIONS

Dialysis and Transplantation, 1994, 23/11, pp. 624-625, 628-635.*

(Continued)

*Primary Examiner*—John Kim
(74) *Attorney, Agent, or Firm*—K&L Gates LLP

(57) ABSTRACT

A multi-part substitution infusion fluid for an extracorporeal blood treatment and methods for using same are provided. Generally, the multi-part substitution fluid comprises a first solution composed of electrolytes but without divalent cations and a second solution comprising divalent cations. Another embodiment includes a third solution comprising a matching citrate/citric acid anticoagulant. The described methods of using the multi-part substitution infusion fluids significantly reduce risks associated with various extracorporeal blood treatments.

10 Claims, 2 Drawing Sheets

U.S. PATENT DOCUMENTS

| | | | |
|---|---|---|---|
| 4,308,255 A | 12/1981 | Raj et al. | |
| 4,336,881 A | 6/1982 | Babb et al. | |
| 4,339,433 A | 7/1982 | Kartinos et al. | |
| 4,489,535 A | 12/1984 | Veltman | |
| 4,574,085 A | 3/1986 | Dolkart et al. | |
| 4,604,379 A | 8/1986 | Twardowski et al. | |
| 4,649,050 A * | 3/1987 | Veech | 424/601 |
| 4,663,166 A | 5/1987 | Veech | |
| 4,668,400 A * | 5/1987 | Veech | 210/647 |
| 4,690,772 A | 9/1987 | Tell et al. | |
| 4,879,280 A | 11/1989 | Seyffart et al. | |
| 4,880,629 A | 11/1989 | Okamoto et al. | |
| 4,886,789 A | 12/1989 | Milner | |
| 4,889,634 A | 12/1989 | El-Rashidy | |
| 4,980,374 A | 12/1990 | Steudle et al. | |
| 5,011,826 A | 4/1991 | Steudle et al. | |
| 5,032,615 A * | 7/1991 | Ward et al. | 514/574 |
| 5,100,677 A * | 3/1992 | Veech | 424/677 |
| 5,178,763 A * | 1/1993 | Delaunay | 210/644 |
| 5,192,459 A | 3/1993 | Tell et al. | |
| 5,211,643 A | 5/1993 | Reinhardt et al. | |
| 5,252,213 A | 10/1993 | Ahmad et al. | |
| 5,296,242 A | 3/1994 | Zander | |
| 5,436,232 A | 7/1995 | Forster et al. | |
| 5,589,197 A | 12/1996 | Shockley et al. | |
| 5,597,805 A | 1/1997 | Breborowicz et al. | |
| 5,616,248 A * | 4/1997 | Schal | 210/647 |
| 5,626,880 A | 5/1997 | Inoue et al. | 424/489 |
| 5,629,025 A | 5/1997 | Shockley et al. | |
| 5,631,025 A | 5/1997 | Shockley et al. | |
| 5,670,176 A | 9/1997 | Martis et al. | |
| 5,674,527 A * | 10/1997 | Inoue et al. | 424/450 |
| 5,698,230 A | 12/1997 | Martis et al. | |
| 5,709,993 A | 1/1998 | Buturovic-Ponikvar | |
| 5,728,681 A * | 3/1998 | Kido et al. | 514/23 |
| 5,827,820 A | 10/1998 | duMoulin et al. | |
| 5,945,129 A | 8/1999 | Knerr et al. | |
| 5,945,449 A | 8/1999 | Purcell et al. | |
| 5,955,450 A | 9/1999 | Breborowicz et al. | |
| 6,017,942 A * | 1/2000 | Bergstrom | 514/399 |
| 6,020,007 A | 2/2000 | Veech | |
| 6,077,836 A | 6/2000 | Milner | |
| 6,083,935 A | 7/2000 | Wu et al. | |
| 6,126,832 A * | 10/2000 | Stone | 210/647 |
| 6,156,797 A | 12/2000 | Kubo et al. | |
| 6,214,802 B1 | 4/2001 | Nakamura et al. | |
| 6,248,726 B1 | 6/2001 | Alsop et al. | |
| 6,251,437 B1 | 6/2001 | Fischbach | |
| 6,277,556 B1 * | 8/2001 | Grode et al. | 435/2 |
| 6,277,815 B1 | 8/2001 | Knerr | |
| 6,306,836 B1 | 10/2001 | Martis et al. | |
| 6,309,673 B1 | 10/2001 | Duponchelle et al. | |
| 6,537,976 B1 * | 3/2003 | Gupta | 514/52 |
| 6,610,206 B1 * | 8/2003 | Callan et al. | 210/646 |
| 6,743,191 B1 * | 6/2004 | Chang | 604/4.01 |
| 7,186,420 B2 * | 3/2007 | Chang et al. | 424/601 |
| 2001/0003794 A1 | 6/2001 | Landry et al. | |

FOREIGN PATENT DOCUMENTS

| | | | |
|---|---|---|---|
| DE | 4211455 C1 | 12/1993 | |
| EP | 76355 A2 | 4/1983 | |
| EP | 86553 B1 | 8/1983 | |
| EP | 115911 B2 | 8/1984 | |
| EP | 153164 B1 | 8/1985 | |
| EP | 399918 B1 | 11/1990 | |
| EP | 417478 B1 | 3/1991 | |
| EP | 456928 B1 | 11/1991 | |
| EP | 602014 B2 | 6/1994 | |
| EP | 0658353 | 6/1995 | |
| EP | 821951 B1 | 2/1998 | |
| GB | 2084484 A | 4/1982 | |
| JP | 3 56010109 A | 2/1981 | |
| JP | 56 128711 A | 10/1981 | |
| JP | 01 242531 A | 9/1989 | |
| JP | 4 03038527 A | 2/1991 | |
| JP | 04 069341 A | 3/1992 | |
| JP | 4 05105633 A | 4/1993 | |
| JP | 4 06105906 A | 4/1994 | |
| JP | 4 06178802 A | 6/1994 | |
| JP | 4 06237991 A | 8/1994 | |
| JP | 4 06245995 A | 9/1994 | |
| JP | 4 06335527 A | 12/1994 | |
| JP | 4 06335528 A | 12/1994 | |
| JP | 4 07059846 A | 3/1995 | |
| JP | 4 08092071 A | 4/1996 | |
| JP | 4 08131542 A | 5/1996 | |
| JP | 4 08164199 A | 6/1996 | |
| JP | 4 08169836 A | 7/1996 | |
| JP | 4 10087478 A | 4/1998 | |
| JP | 4 11114054 A | 4/1999 | |
| JP | 4 11197240 A | 7/1999 | |
| JP | 11279051 A | 10/1999 | |
| JP | 4 11343230 A | 12/1999 | |
| JP | 0 2000037452 A | 2/2000 | |
| JP | 0 2000051348 A | 2/2000 | |
| JP | 0 2000072658 A | 3/2000 | |
| JP | 0 2000140095 A | 5/2000 | |
| JP | 0 2000245826 A | 9/2000 | |
| JP | 0 2000288083 A | 10/2000 | |
| JP | 0 2001054570 A | 2/2001 | |
| WO | WO 90/15612 A1 | 12/1990 | |
| WO | WO 91/10457 A1 | 7/1991 | |
| WO | WO 93/19792 A1 | 10/1993 | |
| WO | WO 93/24108 A1 | 12/1993 | |
| WO | WO 96/01118 A1 | 1/1996 | |
| WO | WO 97/30694 A1 | 8/1997 | |
| WO | WO 98/10745 A1 | 3/1998 | |
| WO | WO 98/29151 A1 | 7/1998 | |
| WO | WO 99/01144 A1 | 1/1999 | |
| WO | 99/07419 | 2/1999 | |
| WO | WO 99/09953 A1 | 3/1999 | |
| WO | WO 99/17762 A1 | 4/1999 | |
| WO | WO 99/20249 A1 | 4/1999 | |
| WO | WO 00/33853 | * | 6/2000 |
| WO | WO 00/33853 A1 | 6/2000 | |

OTHER PUBLICATIONS

Macias, W.L.; "Choice of replacement fluid/dialysate anion in continuous renal replacement therapy"; American Journal of Kidney Diseases, (1996) 28/5 Suppl. 3 (S15-S20); XP000978102; Abstract; p. S15-S16; p. S19.

Ono, K., et al.; "Glucose in the dialysate does not reduce the free amino acid loss during routine hemodialysis of non-fasting patients"; Clinical Nephrology, (1984) 21/2 (106-109); Coden: CLNHBI; XP000856986; Abstract.

Palsson, R., et al.; "Regional citrate anticoagulation in continuous venovenous hemofiltration in critically ill patients with a high risk of bleeding"; Kidney International, (May 1999) 55 (5); 1991-7; XP000978115; Abstract.

Sieberth, H.G.; ["Composition of the rinsing water for extracorporeal hemodialysis in acute and chronic renal failure"]; Zusammensetzung des Waschwassers fur die extracorporate Hamodialyse der akuten und chronischen Niereninsuffizienz; Medizinische Technik, (1974) 94/2 (28-32); Coden: Meteav, XP000856013; Abstract; p. 31, col. 2; Table 1.

Sramek et al., "Continuous venovenoushemodiafiltration (CVVHDF) with citrate anticoagulation in the treatment of a patent with acute renal failure, hypercalcemia, and thrombocytopenia," Intensive Care Med (1998) vol. 24, pp. 262-264.

Lowenthal, et al., "The Cryopreservation of Leukaemia Cells: Morphological and Functional Changes," British Journal of Haematology (1976), vol. 34, pp. 105-117.

Pallone, et al., "Continuous arteriovenous hemofiltration: An in vitro simulation and mathematical model," Kidney International, vol. 33 (1988), pp. 685-698.

T.S. Ing et al., Increasing plasma phosphorus values by enriching with phosphorus the "acid concentrate" of a bicarbonate-buffered dialysate delivery system, The International Journal of Artificial Organs, vol. 15, No. 12, (1992), pp. 701-703.

Palsson et al., "Regional citrate anticoagulation in continuous venovenous hemofiltration in critically ill patents with a high risk of bleeding," Kidney International, vol. 55 (1999), pp. 1991-1997.

Haemodiaysis, Solutions For, European Pharmacopoeia, (1997):0128, pp. 921-927.

Thews et al., "Anatomie Physiologies Pathophysiologie des Menschen," Nebenschilddrusen und Regulation des Calcium- und Phosphat-Haushalts, (1989) cover page and pp. 550-551.

Translation of Opposition Statement—European Patent EP 1 176 969, Application No. 00927004.2, Fresenius, May 18, 2009, pp. 1-18.

Translation of Opposition Statement—European Patent EP 1 176 969, Application No. 00927004.2, Braun, May 20, 2009, pp. 1-4.

Van Stone, J.C.; "Individualization of the dialysate prescription in chronic hemodialysis"; Dialysis and Transplantation, (1994) 23/11 (624-625+628-635); XP000856008; Abstract the Whole Document, p. 634.

* cited by examiner

MULTI-PART SUBSTITUTION INFUSION FLUIDS AND MATCHING ANTICOAGULANTS

RELATED APPLICATIONS

This application is a continuation of U.S. patent application Ser. No. 10/742,137 filed Dec. 19, 2003, now U.S. Pat. No. 7,186,420, which is a continuation-in-part of related U.S. patent application Ser. No. 09/959,543 filed Oct. 23, 2001, now U.S. Pat. No. 6,743,191, which is a Section 371 filing of PCT/EP00/03583 filed Apr. 20, 2000, which claims priority to EP 99201302.9 filed Apr. 26, 1999 the entire contents of which are all herein incorporated by reference in their entirety.

FIELD OF THE INVENTION

The invention relates to multi-part substitution infusion fluids useful for continuous extracorporeal treatment of blood and matching citrate/citric acid anticoagulant solutions. Among these treatments continuous-veno-venous hemofiltration (CVVH) is a widely used technique.

BACKGROUND OF THE INVENTION

Extracorporeal blood treatment is a therapy that is widely used for critically ill patients. Many of these patients suffer from acute renal failure and are treated with continuous renal-replacement therapy (CRRT), a form of extracorporeal blood treatment that is normally performed in the Intensive Care Units (ICU's). In ICUs, CRRT therapy is mostly employed as so-called continuous veno-venous hemofiltration (CVVH) and to a lesser extent as continuous arterio-venous hemofiltration (CAVH) or continuous veno-arterial hemofiltration (CVAH), all of which represent various forms of hemofiltration.

Another form of renal replacement therapy that can be used for patients with renal failure in ICU's is hemodialysis. Pure hemofiltration as a renal-replacement therapy in an ICU can also be combined with hemodialysis as so-called continuous-veno-venous-hemodiafiltration (usually abbreviated as CVVHD or CVVHDF) or as continuous-arterio-venous-hemodiafiltration (usually abbreviated as CAVHD or CAVHDF). The addition of hemodialysis to a hemofiltration therapy implies the addition of a hemodialysis fluid (a so-called 'dialysate') flow, making such combined therapy forms more complex than pure hemofiltration. Hemodialysis usually can only be applied for a few hours per day and is much less effective than pure hemofiltration.

Typically, in extracorporeal treatments such as CVVH, CAVH, CVVHD, CAVHD, CVAH, and hemodialysis an artificial kidney is used. This kidney may be formed of hollow-fibers or of plates, and is connected to a patient's bloodstream by an extracorporeal circuit. In CVVH(D) the supply from and return to the blood of the patient is made via two venous accesses, using a blood pump to provide the driving force for the transport of blood from the patient into the artificial kidney and back to the patient. In CAVH(D), the access which provides the supply of blood to the artificial kidney is made via an artery and the return of the blood to the patient is made via a venous access. In this set-up in most cases blood pumps are generally not used because the arterial blood pressure is used to provide the driving force for the transport of blood, which implies that the blood flow rate directly varies with the blood pressure. Because of better control of blood flow, no risk of arterial catheter-related complications, and higher treatment efficiency, CVVH is preferred above CAVH as renal replacement therapy in ICU's.

In CVVH the patient's blood is passed through the artificial kidney, over a semipermeable membrane. The semipermeable membrane selectively allows plasma water and matter in the blood to cross the membrane from the blood compartment into the filtrate compartment, mimicking the natural filtering function of a kidney. This leads to a considerable loss of fluid from the blood, which is removed as the filtrate in the artificial kidney. Every liter of filtrate fluid that is removed in the artificial kidney, contains a large fraction of the molecules that are dissolved in the plasma, like urea, creatinine, phosphate, potassium, sodium, glucose, amino acids, water-soluble vitamins, magnesium, calcium, sodium, and other ions, and trace elements. The fraction of the molecules that passes the semipermeable membrane depends mainly on the physico-chemical characteristics of the molecules and the membrane. In order to keep the blood volume of the patient at a desired (constant) level, a substitution infusion fluid is added to the blood stream in the extracorporeal circuit, after is has passed through the artificial kidney and before it re-enters the patient's vein.

In a normal CVVH procedure, approximately 50 liters of filtrate are removed per 24 hours, and approximately the same amount of substitution infusion fluid is added into the return of blood side of the extracorporeal circuit. The substitution infusion fluid commonly used is conventional infusion fluid consisting of a physiological saline solution generally only containing about 140 mmol/L of sodium ions, 1.6 mmol/L of calcium ions, 0.75 mmol/L, of magnesium ions, 36 mmol/L of bicarbonate ions, and 110 mmol/L of chloride ions. All forms of hemodialysis or hemodiafiltration therapies are characteristically different from pure hemofiltration by the use of a dialysate fluid flow along the semipermeable membrane side opposite to the blood side. The removal of molecules (clearance) in hemodialysis is dependent on the diffusion of molecules through the semipermeable membrane, while in hemoflitration the molecules are removed by pulling the plasma through the semipermeable membrane, a process that is named convection. With convection the fraction of larger molecules that passes through the semipermeable membrane is much larger than with diffusion. Therefore, all hemodialysis forms of treatment are much less effective in removing larger molecules than pure hemofiltration.

In order to prevent coagulation of the blood during hemofiltration, usually an anticoagulant is added to the blood in the extracorporeal circuit before it enters the artificial kidney. In the past, heparin or fractionated heparin was often used for this purpose. A drawback of the use of heparin, however, is that this use leads to systemic anticoagulation (i.e., anticoagulation of all blood including that within the patient), giving rise to the risk of the occurrence of serious bleeding complications, particularly in seriously ill patients.

Instead of heparin, citrate ions can be used as anticoagulant, as has been proposed for the first time by Pinnick et al., New England Journal of Medicine 1983, 308, 258-263, for hemodialysis. Citrate ions, usually added in the form of trisodium citrate, are believed to bind free calcium ions in the blood, which have a pivotal role in the coagulation cascade.

Citrate ions, added to the blood into the extracorporeal circuit before it enters the artificial kidney, are only active as an anticoagulant in the extracorporeal circuit, whereby the risk of bleeding complications due to systemic anticoagulation is avoided. When citrate ions are applied during hemodialysis forms of treatment, a calcium- and magnesium-free substitution fluid or dialysate is required. Therefore, the application of citrate ions during hemodialysis is more complex than during pure hemofiltration.

Citrate ions are mainly metabolized in skeletal muscle and liver tissue. Only in cases of severe hepatic failure combined with severe shock, or of certain (rare) metabolic diseases, the metabolism of citrate may run short, leading to too high citrate concentrations in the systemic blood circulation, which on its turn may endanger the patient. Accordingly, citrate ions are an attractive anticoagulant for use in pure hemofiltration procedures, especially for use in CVVH treatment in ICU patients.

During hemofiltration, part of the citrate ions is removed from the blood in the artificial kidney. The citrate ions that flow over into the systemic circulation of the patient, are rapidly metabolized to bicarbonate ions in skeletal muscle and liver tissue (about 2.8 molecules bicarbonate are made from 1 citrate molecule). Because trisodium citrate contains on a molar basis three times as many sodium ions as citrate ions, the sodium ions that flow over into the systemic circulation of the patient significantly increases the blood sodium concentration. As a result, hypernatremia and/or an abnormal increase in bicarbonate ions (metabolic alkalosis) may occur. Therefore, replacement of a part of the trisodium citrate by citric acid may reduce the sodium load and, by its acid component, neutralizes part of the bicarbonate generated. Accordingly, a mixture of trisodium citrate with citric acid, is a more attractive anticoagulant for use in hemofiltration procedures than trisodium citrate alone, especially for use in CVVH treatment in ICU patients.

Because citrate ions bind to positively charged metal ions like calcium, magnesium, iron, zinc, copper, and manganese, these ions are also partly removed in the artificial kidney, leading to a net removal of calcium and magnesium ions and other metal ions from the patient's blood. As a result, hypocalcemia and/or hypomagnesemia and/or shortages of other metal ions may be induced in the patient. Especially the hypocalcemia, hypomagnesemia, and/or metabolic alkalosis, may induce life-threatening complications in the patient.

The process of hemofiltration, induces a net removal of phosphate and potassium ions, trace elements, water-soluble vitamins, amino acids and of glucose in the artificial kidney. For example, when during CVVH 50 liters of plasma filtrate per day are removed, it usually contains all of the dissolved urea, creatinine, sodium, potassium, and bicarbonate, and significant amounts of the other dissolved molecules like phosphate, calcium salts, trace elements, water-soluble vitamins, amino acids, and/or glucose. This may lead to significant degrees of hypovolemia, hypophosphatemia, hypokalemia, and shortages of trace elements, water-soluble vitamins, amino acids, and/or glucose, with the risk of deteriorating the patient's condition. Especially the hypophosphatemia may also induce life-threatening complications in the patient. In order to prevent these complications from occurring, it is crucial to return an appropriate volume of substitution infusion fluid per unit of time, containing appropriate amounts of the removed molecules that are needed by the patient.

SUMMARY OF THE INVENTION

The present invention provides one or more substitution infusion fluids combined with matching anticoagulant citrate solutions useful for extracorporeal blood treatments such as, but not limited to, all forms of pure hemofiltration, hemodialysis, hemodiafiltration, combinations of hemofiltration and oxygenation, systemic rewarming, and continuous plasma filtration absorption (CPFA).

In one embodiment of the present invention a single substitution infusion fluid comprising sodium ions, calcium ions, magnesium ions, potassium ions, and optionally glucose, acetate ions and bicarbonate ions in provided.

In another embodiment of the present invention a two part substitution infusion fluid is provided comprising a first substitution infusion fluid comprising electrolytes but excluding magnesium and calcium, and a second aqueous substitution infusion fluid comprising calcium ions and magnesium ions. As used herein electrolytes shall include but are not limited to any one or more of the following: potassium, sodium, chloride and phosphate ions. In an alternative embodiment glucose, potassium and/or phosphate can be included in the first or second substitution infusion fluid.

Both the single and two part substitution infusion fluids of the present invention are generally used with a matching citrate anticoagulant solution comprising trisodium citrate and citric acid.

In one embodiment of the present invention a two part aqueous substitution infusion fluid for an extracorporeal blood treatment is provided having a first aqueous substitution infusion fluid comprising from about 70 mmol/L to about 130 mmol/L sodium ion, about 0.01 mmol/L to about 5 mmol/L of potassium ion, from about 100 mmol to 150 mmol/L chloride ion, about 0.01 mmol to about 1.5 mmol/L phosphate ion and optionally 2 mmol/L to approximately 11.5 mmol/L glucose together with a second aqueous infusion fluid comprising about 10 mmol/L to 35 mmol/L calcium ion, about 2.5 mmol/L to 20 mmol/L magnesium ion and optionally between 0.4 and 0.8 mmol/L of phosphate ions.

Optionally, either substitution infusion fluids of the present invention may also contain between 1.9 and 2.3 mmol/L of calcium ions and/or between 0.5 and 1 mmol/L of magnesium ions.

In another embodiment of the present invention the two part aqueous substitution infusion fluid may also contain iron ions, and/or zinc ions, copper ions, manganese ions, water-soluble vitamins, amino acids and/or other trace elements.

The present invention may also include a matching citrate anticoagulant solution comprising between 19 and 135 mmol/L of citric acid; and between 80 and 550 mmol/L of trisodium citrate.

In another embodiment the matching citrate solution may contain trisodium citrate in an amount of between 106 and 290 mmol/L.

In yet another embodiment of the present invention the matching citrate solution may comprises about 38-39 mmol/L of citric acid and about 211-212 mmol/L of trisodium citrate.

Another aspect of the present invention includes an extracorporeal blood treatment including the steps of providing blood to an artificial kidney via an extracorporeal circuit; adding a citrate/citric acid anticoagulant to the blood prior to entering the artificial kidney, filtering the blood using a semipermeable membrane, adding a substitution fluid back to the filtered blood, returning the filtered blood containing the substitution fluid back to the patient wherein said anticoagulant and said substitution fluid are matched to provide for consistent concentrations of systemic electrolytes in a patient undergoing extracorporeal blood treatment.

Also provided with the present invention is a kit for performing an extracorporeal blood treatment including a citrate/citric acid anticoagulant composition and a matched substitution fluid that provide for consistent concentrations of systemic electrolytes in a patient undergoing extracorporeal blood treatment.

Another embodiment of the present invention is a three part system for hemofiltration of blood including a first aqueous substitution infusion fluid comprising sodium ions, chloride ions and phosphate ions together with a second aqueous infusion fluid comprising calcium ions and magnesium ion together with a matching citrate/citric acid anticoagulant solution.

These and other embodiments of the present invention will be more fully understood reference to the figures and the detailed description that follow.

DETAILED DESCRIPTION OF THE INVENTION

Figure 1:
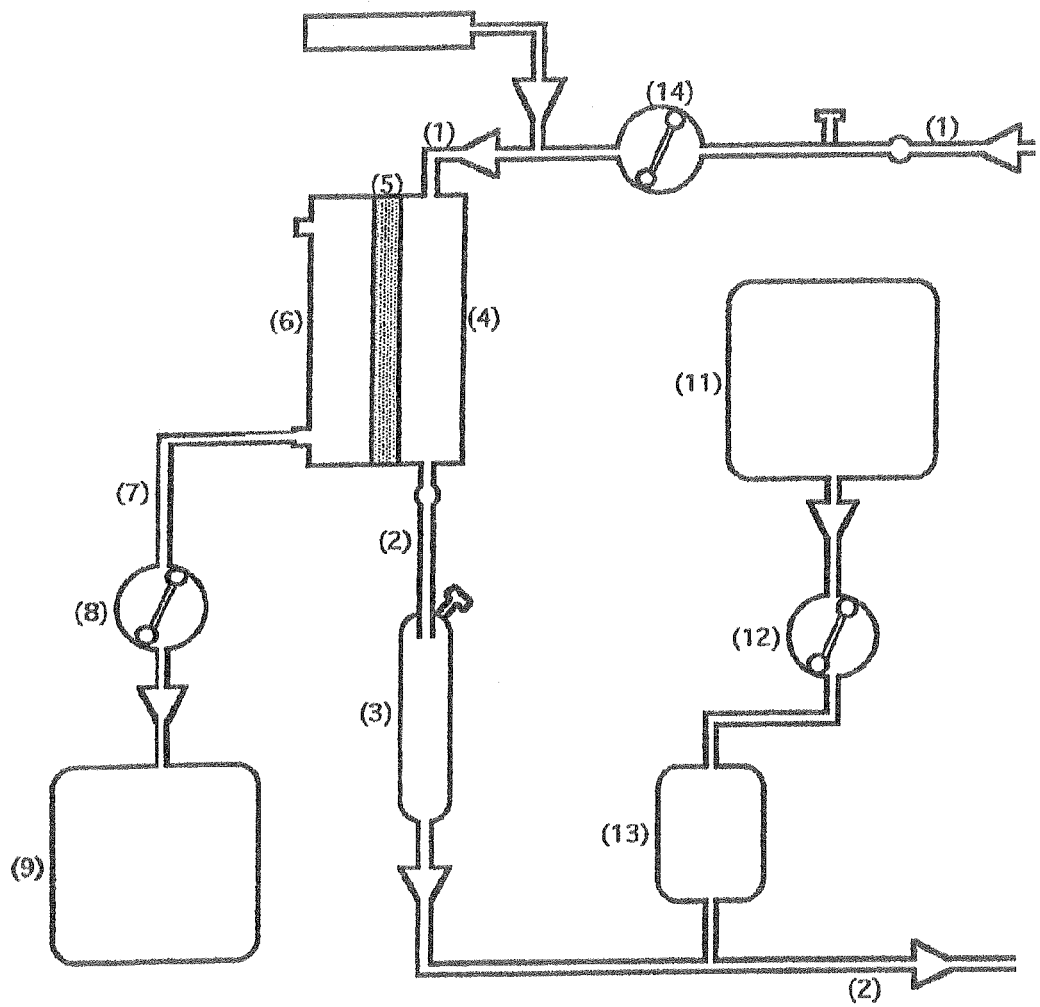
FIG. 1 schematically depicts an exemplary extracorporeal treatment process of the present invention.

As explained above, extracorporeal treatments for use according to the present invention includes but is not limited to various renal-replacement therapies such as pure hemofiltration (CVVH, CAVH, CVAH) hemodialysis, hemodiafiltration, as well as combinations of hemofiltration and oxygenation, systemic rewarming, and CPFA. As used herein term "pure hemofiltration" shall be used to distinguish hemofiltration from hemodiafiltration. Hemodiafiltration combines dialysis with hemofiltration. The present invention provides compositions and methods for preventing complications associated with certain extracorporeal treatments such as continuous-veno-venous-hemofiltration procedures, especially when citrate ions are used as anticoagulant.

Surprisingly, it has been found that these goals may be reached by making use of a substitution infusion fluid of a specific composition. The term "substitution infusion fluid" as used herein may also be referred to as "replacement fluid" or "substitution fluid." No distinction between the claimed substitution infusion fluids and other "replacement fluids" or "substitution fluids" is inferred by the present inventor's choice of terms. Accordingly, in one embodiment the present invention relates to an aqueous substitution infusion fluid for extracorporeal treatments comprising (as used herein mmol/L is "millimoles" of the salt or ion per liter of aqueous substitution infusion fluid) between 0.2 and 1, preferably between 0.5 and 0.9 mmol/L of dihydrogen phosphate ions; between 70 and 130, preferably between 70 and 120 mmol/L of sodium ions; between 1.6 and 2.6, preferably between 1.9 and 2.4 mmol/L of calcium ions; between 0.25 and 1.25, preferably between 0.5 and 1.0 mmol/L of magnesium ions; between 1 and 4, preferably between 1.8 and 3.5 mmol/L of potassium ions; between 3 and 11.5, preferably between 5.5. and 7.5 mmol/L of glucose; below 5.5 mmol/L, preferably between 0 and 3.1 mmol/L of acetate ions; and below 5.5. mmol/L, preferably between 0 and 3.1 mmol/L of bicarbonate ions. This substitution infusion fluid is usually supplemented with chloride ions to achieve a neutral electrochemical balance.

In another embodiment of the present invention the calcium and/or magnesium may be removed form the substitution infusion fluid and provided as a separate infusion fluid. This embodiment has the advantage of being more stable during long term storage than substitution infusion fluids that combine calcium and magnesium with other electrolytes, anions and salts thereof. Moreover, calcium and magnesium-free infusion fluids are more readily adaptable to procedures wherein the substitution fluid is infused prior to filtration where versus post-filtration infusion.

Persons having ordinary skill in the art of extracorporeal blood treatments will realize that balancing fluid input and output is often required to prevent hypertension or hypertension as well as other syndromes associated with dehydration or over-hydration. The multi-part substitution fluids of the present provide a convenient means for achieving optimum fluid balance. The physician having ordinary skill is able to closely monitor fluid intake and electrolyte balance and increase or decrease the total volume of substitution infusion fluids provided the patient as needed. Furthermore, the ordinary skilled physician will combine his/her clinical judgment with laboratory test results. Moreover, the majority of modern extracorporeal blood treatment devices, including but not limited artificial kidneys, have fluid balances integrated into their delivery systems that will alarm an attending physician or nurse should fluid input exceed fluid output or visa versa. Moreover, most extracorporeal blood treatment devices are fully programmable allowing for precise fluid balance regulation and control.

For example, and not intended as a limitation, a two-part aqueous substitution infusion fluid made in accordance with the teachings of the present invention may include a first aqueous substitution infusion fluid having from about 70 mmol/L to about 130 mmol/L sodium ion, about 2 mmol/L to about 10 mmol/L of glucose, about 0.01 mmol/L to about 5 mmol/L of potassium ion, from about 100 mmol to 150 mmol/L chloride ion and about 0.01 mmol to about 1.5 mmol/L phosphate ion.

The first substitution infusion fluid described above could then be used in combinations with a second aqueous infusion fluid having about 10 mmol/L to 34 mmol/L calcium ion, about 2.5 mmol/L to 20 mmol/L magnesium ion and 30 mmol/L to about 100 mmol/L of chloride ion.

Moreover, in another embodiment the substitution infusion fluids of the present invention (both the one-part and two-part substitution infusion fluids) may be used with a matching citrate solution. The same citrate solution is used regardless of whether a one part or two-part substitution infusion fluid is used. Thus by using the specific substitution infusion fluid together with a matching citrate anticoagulant solution in an extracorporeal blood treatment procedure, the concentrations of potassium, phosphate, calcium, magnesium, bicarbonate ions, and glucose remain substantially within acceptable ranges. In most cases, the concentrations of these ions and glucose remain more or less constant in the systemic blood of the patient undergoing, for example, hemofiltration. Consequently, the chances of the occurrence of the problems encountered in hemofiltration to date are significantly reduced, if not eliminated altogether. Particularly, the chances of the above-indicated complications including electrolyte or acid-base abnormalities and/or sever bleeding are significantly reduced.

The substitution infusion fluids according to the present invention may be conveniently prepared by dissolving salts in water in such amounts that the desired concentrations are reached, as is well within the expertise of the normal person skilled in the art. During preparation, it is desired that a sterile environment is maintained. Accordingly, the substitution infusion fluids preferably are sterile, according to the European Pharmacopeia or United States (US) Pharmacopeia, thereby avoiding the risk of infections in a patient when the fluids are used during hemofiltration.

Typically, substitution infusion fluids are hypotonic. Exemplary values are between 200 and 270 mOsm/L. Nevertheless, it has been found that the fluid is well tolerated by patients when it is used in a hemofiltration procedure. It has been found that the hypotonicity is in fact beneficial by compensating for the hypertonicity induced at the arterial side of the extracorporeal circuit by the anticoagulant. The result is that the blood that is returned into the patient's blood stream has substantially normal (physiological) osmolarity.

Surprisingly, it has also been found that the prevention of the occurrence of the above-described complications may further avoided by making use of a matching citrate anticoagulation fluid in accordance with the teachings of the present invention. Accordingly, the invention also relates to an aqueous citrate anticoagulation fluid for extracorporeal treatments comprising between 19 and 135 mmol/L of citric acid; and between 80 and 550 mmol/L of trisodium citrate, preferably between 106 and 290 mmol/L of trisodium citrate.

By using the citrate anticoagulation infusion fluid according to the invention in an extracorporeal treatment, the blood is effectively anticoagulated within the extracorporeal circuit and not within the systemic circulation of the patient and the concentrations of sodium, calcium, magnesium, and bicarbonate ions remain substantially within ranges of which it is accepted that they lead not to unacceptable risk of complications within the patient. This citrate anticoagulant solution could be used in any appropriate extracorporeal blood treatment and is especially useful during all kinds of pure hemofiltration procedures in combination with the matching substitution infusion fluids according to the present invention. In one exemplary embodiment, such solution may include, for example, a one part substitution infusion fluid comprising about 117 mmol/L-129 mol/mL of sodium ions, about 2.3 mol/L of calcium ions, about 2.5 mmol/L-3.0 mmol/L of potassium ions, about 0.8 mmol/L of phosphate ions, about 0.9 mmol/L of magnesium ions, about 6.5 mmol/L-7.1 mmol/L of glucose, less than 5.5 mmol/L of acetic acid, and chloride ions to keep electrochemical balance. Moreover, it may be desirable to add about 0.0 mmol/L to about 5.5 mmol/L, of acetate ion to prevent the formation of calcium phosphate sedimentation in the one part substitution infusion fluid. In other embodiments, for example, glucose and/or acetic acid and/or phosphate can be omitted, as well as concentrations of other ingredients can be adjusted up or down as necessary.

In another embodiment of the present invention a two-part substitution infusion fluid is used in combination with the matching citrate solution. Such two-part substitution infusion fluid for use in various extracorporeal treatments will comprise a first infusion substitution fluid including electrolytes, but excluding calcium and magnesium, and a second infusion fluid comprising calcium and magnesium. In one example, the two part substitution infusion fluid may comprise a first substitution infusion fluid comprising between 70 and 130 mmol/L sodium, between 0.01 and 5 mmol/L potassium, up to 150 mmol/L chloride and between 0.01 and 1.5 mmol/L phosphate; and a second substitution infusion fluid may comprise between 10-35 mmol/L calcium and between 2.5 to 20 mmol/L magnesium ions. Optionally, the first substitution infusion fluid may also comprise between 2 and 11.5 mmol/L of glucose. In other embodiments, between 0.4 and 0.8 mmol/L of phosphate ions may be added to either the first of the second solution.

In one embodiment of the present invention calcium ion provided in the form of a calcium salt selected from the group consisting of calcium glubionate, calcium chloride and calcium gluconate and magnesium ion is provided in the form of a magnesium salt selected from the group consisting magnesium sulfate, magnesium chloride, magnesium gluconate and magnesium gluconate.

In a preferred embodiment a two part substitution infusion fluids is used in combination with a matching anticoagulant citrate solution. The two part substitution infusion fluid comprising a first substitution infusion fluid comprising about 117 mmol/L sodium, about 6.5 mmol/L glucose, about 2.6 mmol/L potassium, about 15 mmol/L-140 mmol/L chloride and about 0.8 mmol/L phosphate; and a second substitution infusion fluid comprising about 15-25 mmol/L calcium, about 10-12 mmol/L magnesium ions. In a preferred embodiment, the second substitution infusion fluid comprises from about 14-16 mmol/L calcium and from about 10-11 mmol/L magnesium.

It has been found that when a two part substation fluid of this type is used in combination with a matching solution of trisodium citrate consisting of about 106-290 mmol/L trisodium citrate as an anticoagulant, the concentrations of the indicated ions in the patient's blood remain substantially within the physiological range throughout the examplary pure hemofiltration procedure.

In a preferred embodiment, the present citrate anticoagulation solution for pure hemofiltration treatment is an aqueous solution meeting the above requirements, comprising about 38 mmol/L of citric acid and about 212 mmol/L of trisodium citrate. This citrate anticoagulation solution is preferably in combination with a matching two part substitution infusion fluid as disclosed above.

By way of example, the invention will now be described in more detail while referring to FIG. 1 which illustrates the process of hemofiltration by CVVH. Referring to FIG. 1, blood is extracted from a vein of a patient and transported to an artificial kidney (4, 5, 6) via the arterial side (1) of an extracorporeal circuit (1, 2) by the driving force of a blood pump (114). Anticoagulant, a matching citrate solution, is added to the blood between the blood pump (14) and the artificial kidney (10). In another embodiment, the citrate anticoagulant can be added downstream of the blood pump (14). Optionally, an additional pump can be used to assist the flow of the citrate anticoagulant.

In the artificial kidney, the blood is filtered over a semipermeable membrane (5). The filtrate is removed from the filtrate compartment of the artificial kidney (6) via connecting tubing (7). A pump (8) takes care of the transport of filtrate into a collection reservoir (9).

The retentate blood is transported back from the retentate compartment of the artificial kidney (4) to the patient's blood stream via the venous side (return side) of the extracorporeal circuit (2), after passage of an airtrap (3). The airtrap serves to remove all air bubbles from the blood before it is returned into the patient's blood stream. Preferably, the blood is returned into the patient's blood stream at the same place as at which it was extracted, e.g., by way of a double-lumen venous catheter.

Before the blood is returned to the patient, the substitution infusion fluid is added from a reservoir (11), via a pump (12) and a heater (13). The heater ensures that the fluid ultimately entering the patient's body is substantially equal to the patient's body temperature, thus making the entire procedure substantially less uncomfortable.

Figure 2:
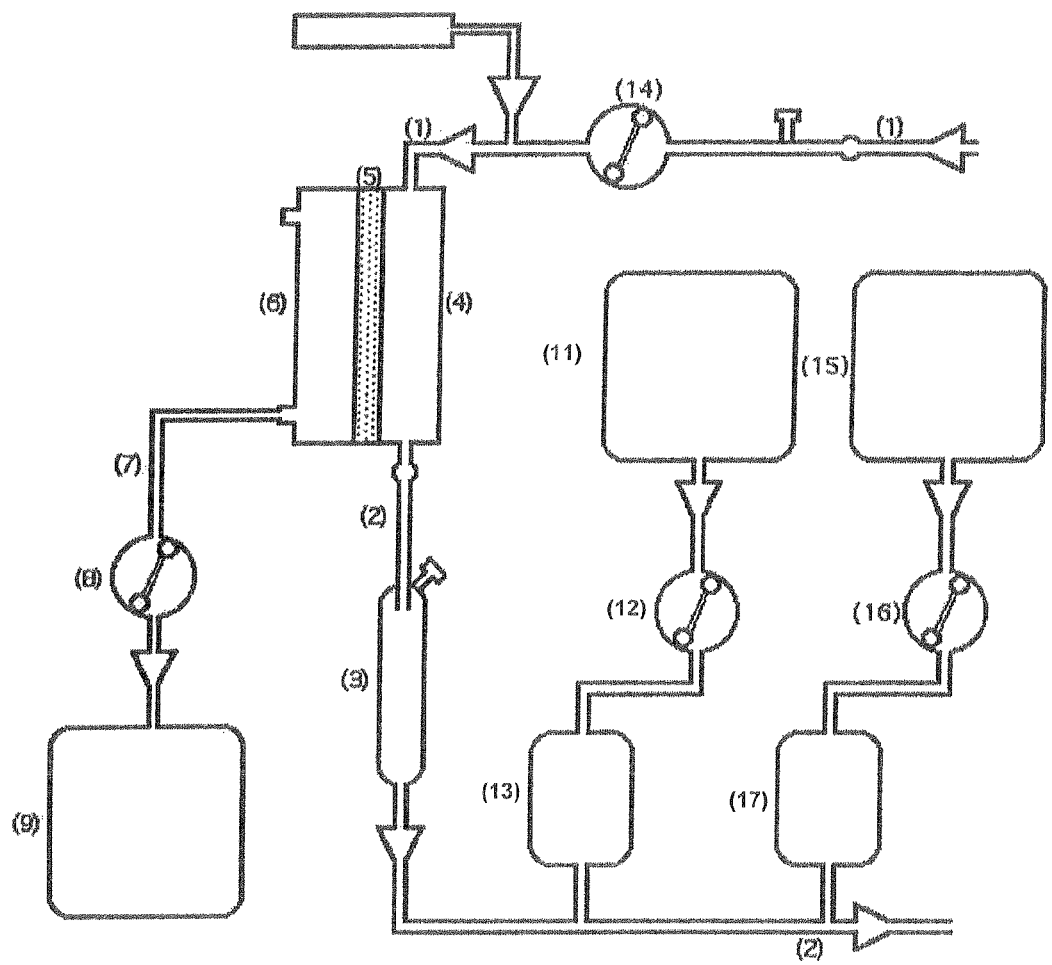
FIG. 2 schematically depicts an exemplary alternative extracorporeal treatment of the present invention.

FIG. 2 depicts another embodiment wherein a two part substation infusion fluid is used necessitating two reservoirs (11) and (15) which supply first substitution infusion fluid and the second substation infusion fluid via separate pumps (12) and (16) and heaters (13) and (18).

During the procedure, the amount of filtrate collected in the reservoir (9) is determined accurately, e.g., by weighing (device not shown). The amount of substitution infusion fluid added to the blood is adapted to this amount. This makes it possible to make sure that an exactly predetermined volume of fluid is returned to the patient's body (2), matching the originally extracted volume therefrom or adapted to the fluid balance needed in a particular patient (1). The flow through pumps (8) and (12) or (16) are accordingly precisely adjusted to one another. Typically, the substitution infusion fluid is administered (infused) into the blood at a rate of between 8 and 80 ml/min per 200 ml/min blood. In practice, alerting means, such as an audible alarm, are often provided for alerting nursing personnel should an interruption of the blood, filtrate, or substitution flow occur. Typically, said specific anticoagulation fluid of trisodium citrate and citric acid is infused into the blood at a rate of between 1.3 and 4 ml/min per 200 ml/min blood.

We claim:

1. A three part system for extracorporeal blood treatment comprising:
   - a first aqueous infusion fluid comprising sodium ion, potassium ion, chloride ion and phosphate ion;
   - a second aqueous infusion fluid comprising calcium ion and from about 2.5 mmol/L to about 20 mmol/L of magnesium ion; and
   - a citrate anticoagulant solution comprising from about 19 mmol/L to about 135 mmol/L of citric acid and from about 80 mmol/L to about 550 mmol/L of trisodium citrate.

2. The three part system for extracorporeal blood treatment according to claim 1, wherein the second aqueous infusion fluid has from about 10 mmol/L to about 35 mmol/L of the calcium ion.

3. The three part system for extracorporeal blood treatment according to claim 1, wherein the first aqueous infusion fluid has from about 70 mmol/L to about 130 mmol/L of the sodium ion.

4. The three part system for extracorporeal blood treatment according to claim 1, wherein the first aqueous infusion fluid has from about 0.01 mmol/L to about 5 mmol/L of the potassium ion.

5. The three part system for extracorporeal blood treatment according to claim 1, wherein the first aqueous infusion fluid has from about 100 mmol/L to about 150 mmol/L of the chloride ion.

6. The three part system for extracorporeal blood treatment according to claim 1, wherein the first aqueous infusion fluid has from about 0.01 mmol/L to about 1.5 mmol/L of the phosphate ion.

7. The three part system for extracorporeal blood treatment according to claim 1, wherein the first aqueous infusion fluid further comprises from about 2 mmol/L to about 11.5 mmol/L of glucose.

8. The three part system for extracorporeal blood treatment according to claim 7, wherein the second aqueous infusion fluid further comprises from about 30 mmol/L to about 100 mmol/L selected from a group consisting of sulphate, gluconate, glubionate and chloride ion.

9. The three part system for extracorporeal blood treatment according to claim 1, wherein the first aqueous infusion fluid further comprises amino acids and/or trace elements.

10. The three part system for extracorporeal blood treatment according to claim 1 further comprising ions selected from a group consisting of iron, zinc, copper and manganese.

* * * * *